United States Patent
Sa et al.

(10) Patent No.: US 11,604,840 B1
(45) Date of Patent: Mar. 14, 2023

(54) SYSTEM AND METHOD FOR PROCESSING REGULATORY SUBMISSIONS

(71) Applicant: Veeva Systems Inc., Pleasanton, CA (US)

(72) Inventors: Rolando Sa, Lebanon, NJ (US); Uri Reich, Hamden, NJ (US); Richard Merrick, Dresher, PA (US); Hong Fai Chan, Markham (CA)

(73) Assignee: Veeva Systems Inc., Pleasanton, CA (US)

( * ) Notice: Subject to any disclaimer, the term of this patent is extended or adjusted under 35 U.S.C. 154(b) by 506 days.

(21) Appl. No.: 16/252,541

(22) Filed: Jan. 18, 2019

(51) Int. Cl.
| | |
|---|---|
| *G06Q 30/00* | (2012.01) |
| *G06F 16/17* | (2019.01) |
| *G06F 16/11* | (2019.01) |
| *G06F 16/93* | (2019.01) |
| *G06Q 30/018* | (2023.01) |
| *G16H 15/00* | (2018.01) |
| *G06F 9/54* | (2006.01) |

(52) U.S. Cl.
CPC .............. *G06F 16/94* (2019.01); *G06F 9/542* (2013.01); *G06F 16/113* (2019.01); *G06F 16/1734* (2019.01); *G06Q 30/018* (2013.01); *G16H 15/00* (2018.01)

(58) Field of Classification Search
None
See application file for complete search history.

(56) References Cited

U.S. PATENT DOCUMENTS

| | | | |
|---|---|---|---|
| 2007/0185751 A1* | 8/2007 | Dempers | G16H 70/40 705/7.29 |
| 2012/0158604 A1* | 6/2012 | Lawton | G06Q 10/109 705/317 |
| 2013/0006702 A1* | 1/2013 | Wu | G06Q 10/10 705/7.28 |
| 2020/0175110 A1* | 6/2020 | Snyder | G06F 40/279 |
| 2021/0209549 A1* | 7/2021 | Bornstein | G06Q 30/012 |

* cited by examiner

*Primary Examiner* — Eddy Cheung

(57) ABSTRACT

Systems and methods for submitting regulatory documents, from authoring through uploading to a health authority gateway. It may continuously publish documents into a submission archive as documents become associated to the content plan and as related content or attributes are updated. It may continuously validate submission components by applying validation rules defined by a health authority to report non-conforming validation results during the publishing process. It may allow users to review and resolve validation errors and warnings by reporting information to users on an ongoing basis to help reduce end-stage reconciliation.

20 Claims, 14 Drawing Sheets

Search

| Library | Tasks | Submission Structure | Reports | Dashboard |

NDA 8700   Binding   Add

Search Current Binder

☐ 1. Administrative Information
☐ 2. Common Technical Document Summaries
    2.2 Introduction
    2.3 Quality Overall Summary
    2.4 Nonclinical Overview
    2.5 Clinical Overview
        - Clinical Overview 12345
    2.6 Clinical Summary
☐ 3. Quality
☐ 4. Nonclinical Study Reports
☐ 5. Clinical Study reports VIEWS
- All Structure
- Recent Structure
- My Structure
- Favorites

FILTERS

PRODUCT
- All
- Coldcap
- R

DOCUMENT TYPES
-

STATUS
- All
- Draft
- Planned
- In Approval
- In Review

| Registration | Application | Products | Submission Structure | Reports | Dashboard |

Search

VIEWS
All Registrations
Recent Registration

FILTERS
- Country
- Pharmaceutical Product

| Registrations or License No. | Country | Registration Status | Product | Presentation |
|---|---|---|---|---|
| AU Coldcap 390 | Australia | Planned | Coldcap | 15mg with 8ml diluent |
| BR Coldcap 125 | Brazil | Marketed | Coldcap | 15mg with 8ml diluent |

| Registration | Application | Submission Structure | Reports | |
|---|---|---|---|---|
| | | | | Search |
| | | | | Dashboard |

What is it Registered?

| Registrations or License No. | Registration Holder | Registration Status | Registration Status Date | Application No. | Product Name | Product Detail | Manufacturer Dosage Form |
|---|---|---|---|---|---|---|---|
| AU Coldcap 390 | | Planned | 1/5 | 089 | Coldcap | 15mg | with 8ml diluent |
| BR Coldcap 125 | | Marketed | 2/2 | 121 | Coldcap | 15mg | with 8ml diluent |

[Registration] [Application] [Products] [Library] [Viewer] [Tasks] [Dashboard] [Reports] [Loader]

Search: _____

Application Selector: _____

SubmissionArchive Viewer: NDA 3001 Submissions

VIEWS
- All Submissions

FILTERS
- Submission ID
- Submission Type
  - All
  - Original Application
  - Annual Report ☐ Module 1 Administrative Information
☐ Module 2 Summaries
  ☐ 2.2 Introduction to summary
  ☐ 2.3 Quality Overall Summary
    ☐ Introduction
    ☐ Introduction to Quality Overall Summary
    ☐ Drug Substance
      ☐ TC03-doc-1 Original
      ☐ TC03-doc1-Appendant1-Replacement  — 1101
☐ Module 3 Quality
☐ Module 4 Nonclinical Study Reports
☐ Module 5 Clinical Study Reports TC03-doc-1-Appendant1-Replacement
Title: TC03-doc-1-Appendant1-Replacement
ID: ID303
Operation: Replace
Modified File:
Xlink Type: Simple
Checksum Type:
Checksum:
Substance:
Manufacturer:

5020 – Medium – Cover Letter

Details

Name         5020 – Medium – Cover Letter

Status       Active

Validation code    5020

Lifecycle    Validation results

Lifecycle State    Unsuccessful

Application    nda1234

Submission    nda1234 - 0000

Content Plan Item    1.2 Cover Letter

Content Plan Item    1.2 Cover Letter 1

Published Document    Cover Letter V0.2

FIG. 13

SYSTEM AND METHOD FOR PROCESSING REGULATORY SUBMISSIONS

BACKGROUND

The subject technology relates generally to content management systems, and more particularly to processing regulatory submissions to health authorities.

Regulatory information management (RIM) has become a major focus among pharmaceutical companies, since it is important to meet their regulatory and compliance obligations, and improve their business processes and productivity across the global. For a pharmaceutical company, the regulatory information may include, e.g., safety reporting, product registrations, central and local requirements, submissions to health authorities, and health authority information management.

Pharmaceutical companies submit electronic documents to health authorities (such as the U.S. FDA) to gain approval for their products. Health authorities publish validation criteria defining the requirements for technical acceptance of a submission (e.g., an Electronic Common Technical Document ("eCTD")) with varying severity levels. The validation criteria are typically updated multiple times each year and unique to a health authority or region. Validation criteria may be broken into two main aspects: structural validation covering aspects of a submission that impact the XMLs or file/folder level information (e.g., schema validation), and file validation covering aspects of the submission that are within various files (e.g., PDF hyperlinks functional and valid).

The validation of a submission based on health authority requirements is a recommendation from all health authorities and a requirement for most. If a submission fails validation at the health authorities, companies risk a technical refusal to file requiring companies to correct and resubmit, delaying a product's review and approval.

However, regulatory information is traditionally captured in a multitude of disconnected central and local systems, and users have to move the documents to be submitted among these systems. Therefore, it is desirable to provide a more efficient publishing and validation process.

SUMMARY

The disclosed subject matter relates to a method for managing submission of a document with a content management system. The content management system comprises a content management server and a plurality of repositories. The method comprises creating an event in the content management system in response to a change; determining if a first submission is needed based on type of the change; creating a first object in the content management system to define the first submission when the first submission is needed; creating a first content plan for the first submission in the content management system to define content to be submitted based on the change; associating a first component, which is in the scope of the defined content to be submitted, with the first submission; publishing the first component of the first submission to a submission archive in the content management system; and validating the first component against a first validation criterion, wherein the first validation criterion is based on a regulatory requirement.

BRIEF DESCRIPTION OF THE DRAWINGS

FIG. 7 illustrates an example submission structure user interface according to one embodiment of the present invention.

FIG. 9 illustrates an example registration user interface according to one embodiment of the present invention.

FIG. 10 illustrates an example registration report user interface according to one embodiment of the present invention.

FIG. 11 illustrates an example submission archive user interface according to one embodiment of the present invention.

FIG. 13 illustrates an example validation result according to one embodiment of the present invention.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, well-known structures and components are shown in block diagram form in order to avoid obscuring the concepts of the subject technology.

The present invention uses a content management system to provide an end-to-end solution for submitting regulatory documents, from authoring through uploading to a health authority gateway.

It may enable creation of cross-document links within the content management system by extending link annotations in the content management system to allow link to a document, named destination and migrating anchor across versions.

It may extend content plans to support XML requirements by extending current content plan templates and content plans to support XML specific attributes and allowing users to target desired output format.

It may provide the capability to continuously publish documents into a submission archive as documents become associated with the content plan and as related content or attributes are updated.

It may continuously validate submission components by applying validation rules defined by a health authority to report non-conforming validation results during the publishing process.

It may allow users to review and resolve validation errors and warnings by reporting information to users on an ongoing basis to help reduce end-stage reconciliation.

It may allow users to upload submissions to a health authority gateway directly by providing users with a simplified interface for transmitting published submission to the health authority gateway.

It may allow users to review and resolve gateway responses by receiving responses from the health authority gateway and parsing the messages to determine the transmission outcome.

Figure 1:
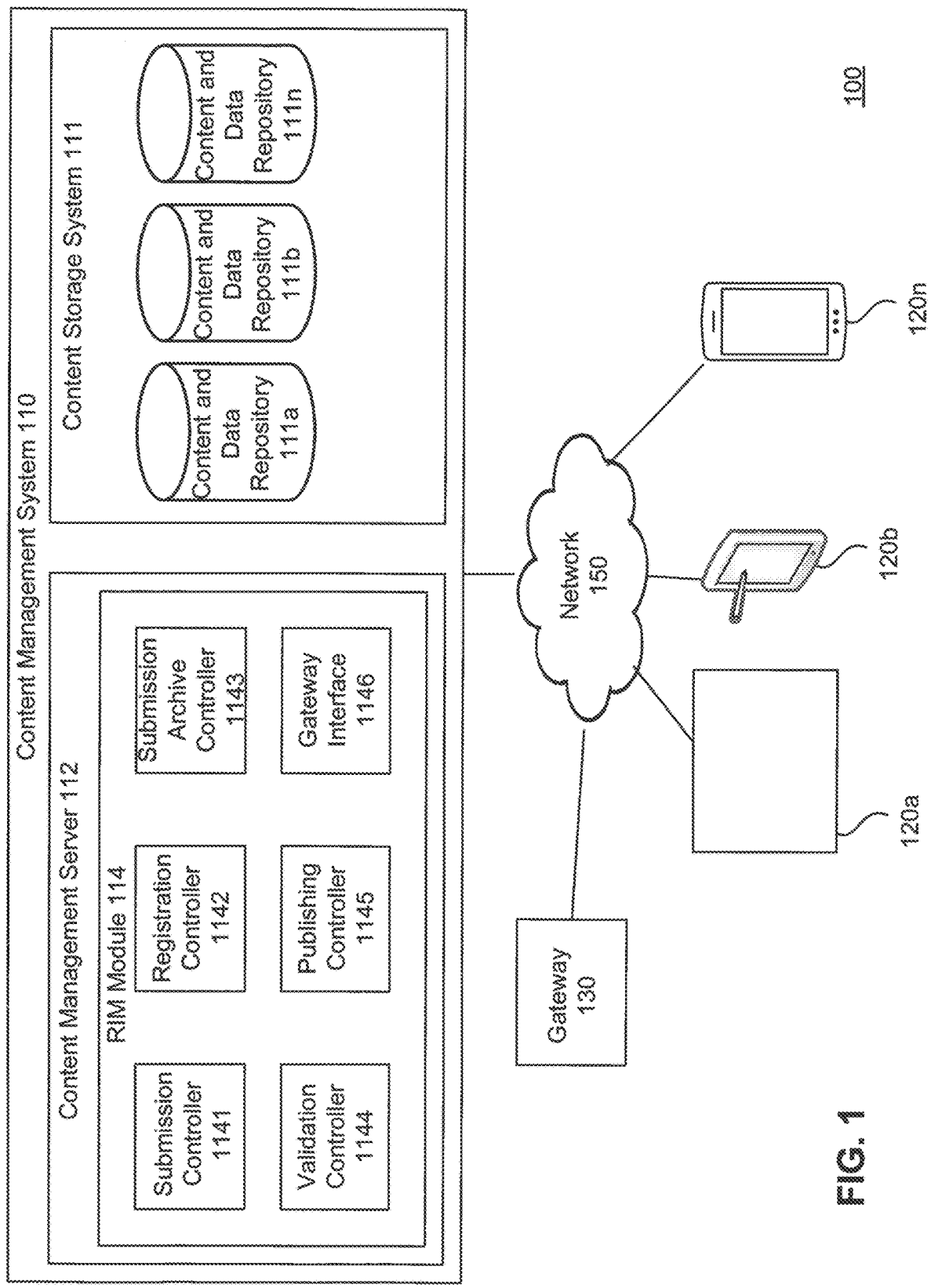
FIG. 1 illustrates an example high level block diagram of a regulatory information management architecture wherein the present invention may be implemented.

FIG. 1 illustrates an example high level block diagram of an enterprise content management architecture 100 wherein the present invention may be implemented. The enterprise may be a business, or an organization. As shown, the architecture 100 may include a content management system 110, and a plurality of user computing devices 120a, 120b, . . . 120n, coupled to each other via a network 150. The content management system 110 may include a content storage system 111 and a content management server 112. The content storage system 111 may have one or more content and data repositories, e.g., 111a, 111b, and 111n. The network 150 may include one or more types of communication networks, e.g., a local area network ("LAN"), a wide area network ("WAN"), an intra-network, an inter-network (e.g., the Internet), a telecommunication network, and peer-to-peer networks (e.g., ad hoc peer-to-peer networks), which may be wired or wireless.

The user computing devices 120a-120n may be any machine or system that is used by a user to access the content management system 110 via the network 150, and may be any commercially available computing devices including laptop computers, desktop computers, mobile phones, smart phones, tablet computers, netbooks, and personal digital assistants (PDAs).

The content management server 112 is typically a remote computer system accessible over a remote or local network, such as the network 150. The content management server 112 may include a regulatory information management module 114. The regulatory information management module 114 may have a submission controller 1141, a registration controller 1142, a submission archive controller 1143, a validation controller 1144, a publishing controller 1145, and a gateway interface 1146, which will be described in detail with reference to FIG. 3.

The content storage system 111 may store content that user computing devices 120a-120n may access. Each content repository (e.g., 111a, 111b, or 111n) may store a specific category of content, and allow users to interact with its content in a specific business context.

In one implementation, the repository 111a may store a submissions library for regulatory content related to submissions, which may include information and submissible documents and data for the generation of submission structures, and the planning, authoring and collection of required documents. Within the submissions library, users may quickly find information they are looking for through search and filtering. The user may find drug documentation related to a product or a geographic region. The repository 111a may also store information about review and approval flow, status of documents and a filing, and dashboard reports, giving users the ability to manage the overall process.

In one implementation, the repository 111a may also store regulatory information related to product registration, which may include product registration information and health authority interactions. The product registration information may include, e.g., the associated product information, application information, application date, registration details, key registration dates, marketing status, and marketing details. In one example, the user may see all the global registrations and their status in one report. The health authority interactions may include bidirectional interactions with health authorities globally, including correspondence, commitments and queries.

In one implementation, the repository 111a may also store information for a submission archive, which may include a customer's complete global history of regulatory submissions and correspondence.

In one implementation, the repository 111a may also store source documents for the regulatory information management system.

Although the submissions library, regulatory information related to product registration, submission archive, and source documents for the regulatory information management system are shown to be stored in one repository, it should be understood that they might be stored in multiple repositories.

The gateway 130 may be a web portal of a health authority.

In one implementation, the content management system 110 may be a multi-tenant system where various elements of hardware and software may be shared by one or more customers. For instance, a server may simultaneously process requests from a plurality of customers, and the content storage system 111 may store content for a plurality of customers. In a multi-tenant system, a user is typically associated with a particular customer. In one example, a user could be an employee of one of a number of pharmaceutical companies which are tenants, or customers, of the content management system 110.

In one embodiment, the content management system 110 may run on a cloud computing platform. Users can access content on the cloud independently by using a virtual machine image, or purchasing access to a service maintained by a cloud database provider.

In one embodiment, the content management system 110 may be provided as Software as a Service ("SaaS") to allow users to access the content management system 110 with a thin client.

Figure 2:
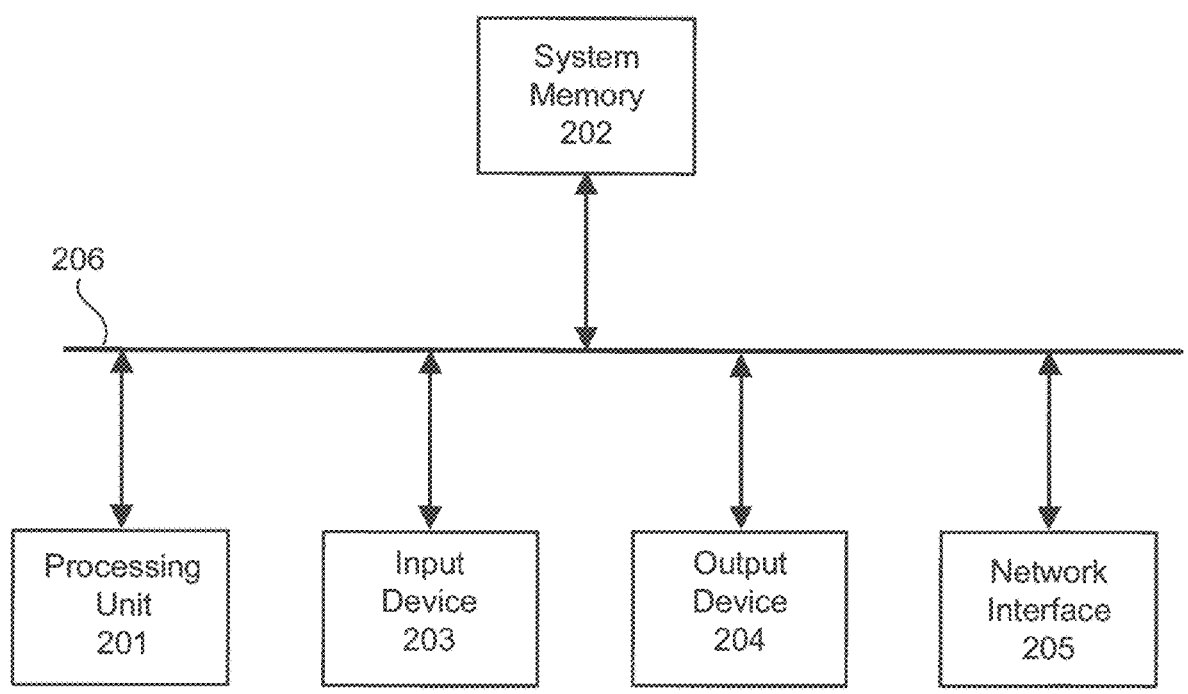
FIG. 2 illustrates an example high level block diagram of a computing device.

FIG. 2 illustrates an example block diagram of a computing device 200 which can be used as the user computing devices 120a-120n, and the content management server 112 in FIG. 1. The computing device 200 is only one example of a suitable computing environment and is not intended to suggest any limitation as to scope of use or functionality. The computing device 200 may include a processing unit 201, a system memory 202, an input device 203, an output device 204, a network interface 205 and a system bus 206 that couples these components to each other.

The processing unit 201 may be configured to execute computer instructions that are stored in a computer-readable medium, for example, the system memory 202. The processing unit 201 may be a central processing unit (CPU).

The system memory 202 typically includes a variety of computer readable media which may be any available media accessible by the processing unit 201. For instance, the system memory 202 may include computer storage media in the form of volatile and/or nonvolatile memory such as read only memory (ROM) and/or random access memory (RAM). By way of example, but not limitation, the system memory 202 may store instructions and data, e.g., an operating system, program modules, various application programs, and program data.

A user can enter commands and information to the computing device 200 through the input device 203. The input device 203 may be, e.g., a keyboard, a touchscreen input device, a touch pad, a mouse, a microphone, and/or a pen.

The computing device 200 may provide its output via the output device 204 which may be, e.g., a monitor or other type of display device, a speaker, or a printer.

The computing device 200, through the network interface 205, may operate in a networked or distributed environment using logical connections to one or more other computing devices, which may be a personal computer, a server, a router, a network PC, a peer device, a smart phone, or any other media consumption or transmission device, and may include any or all of the elements described above. The logical connections may include a network (e.g., the network 150) and/or buses. The network interface 205 may be configured to allow the computing device 200 to transmit and receive data in a network, for example, the network 150. The network interface 205 may include one or more network interface cards (NICs).

Figure 3:
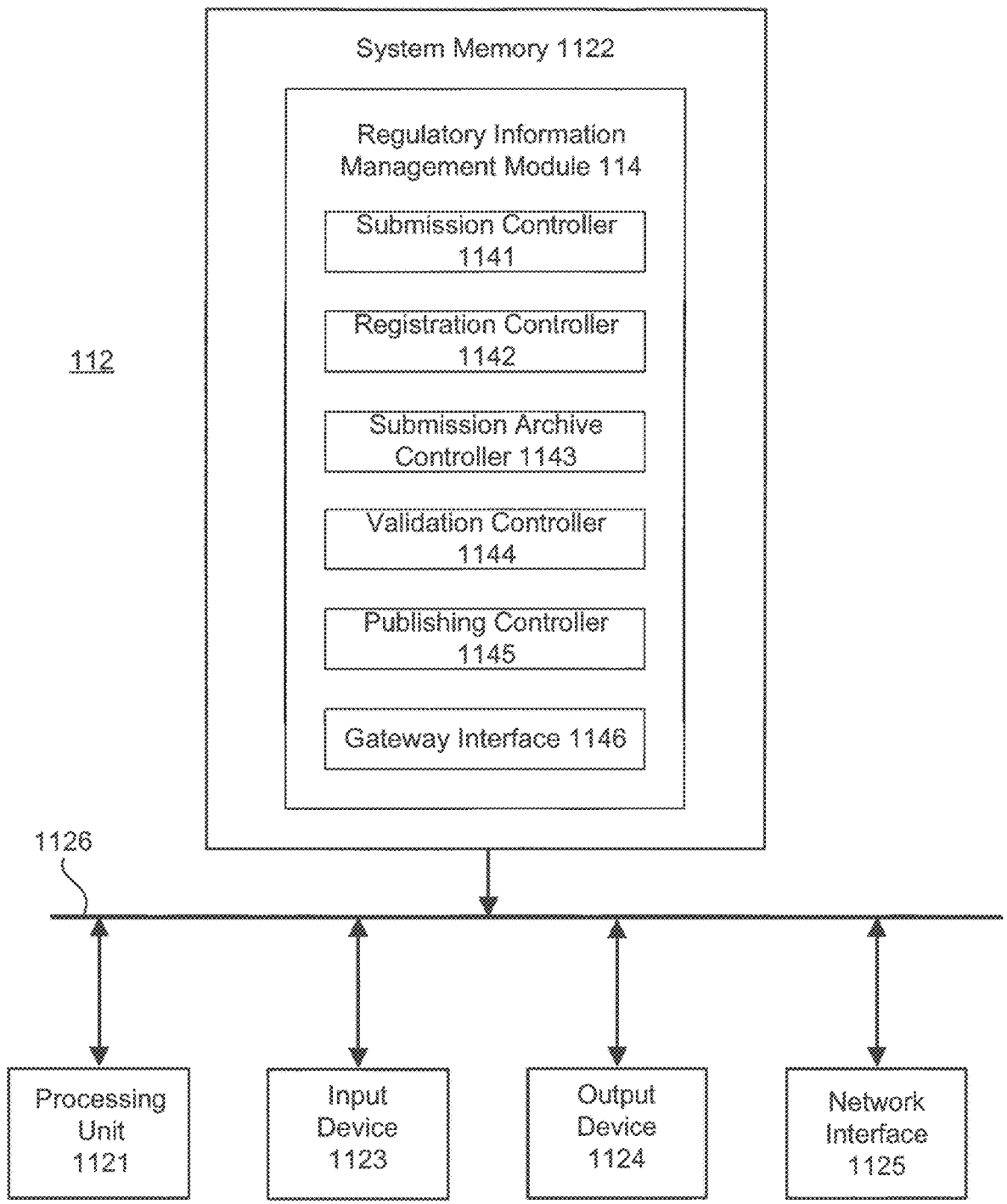
FIG. 3 illustrates an example high level block diagram of the content management server according to one embodiment of the present invention.
Figure 4:
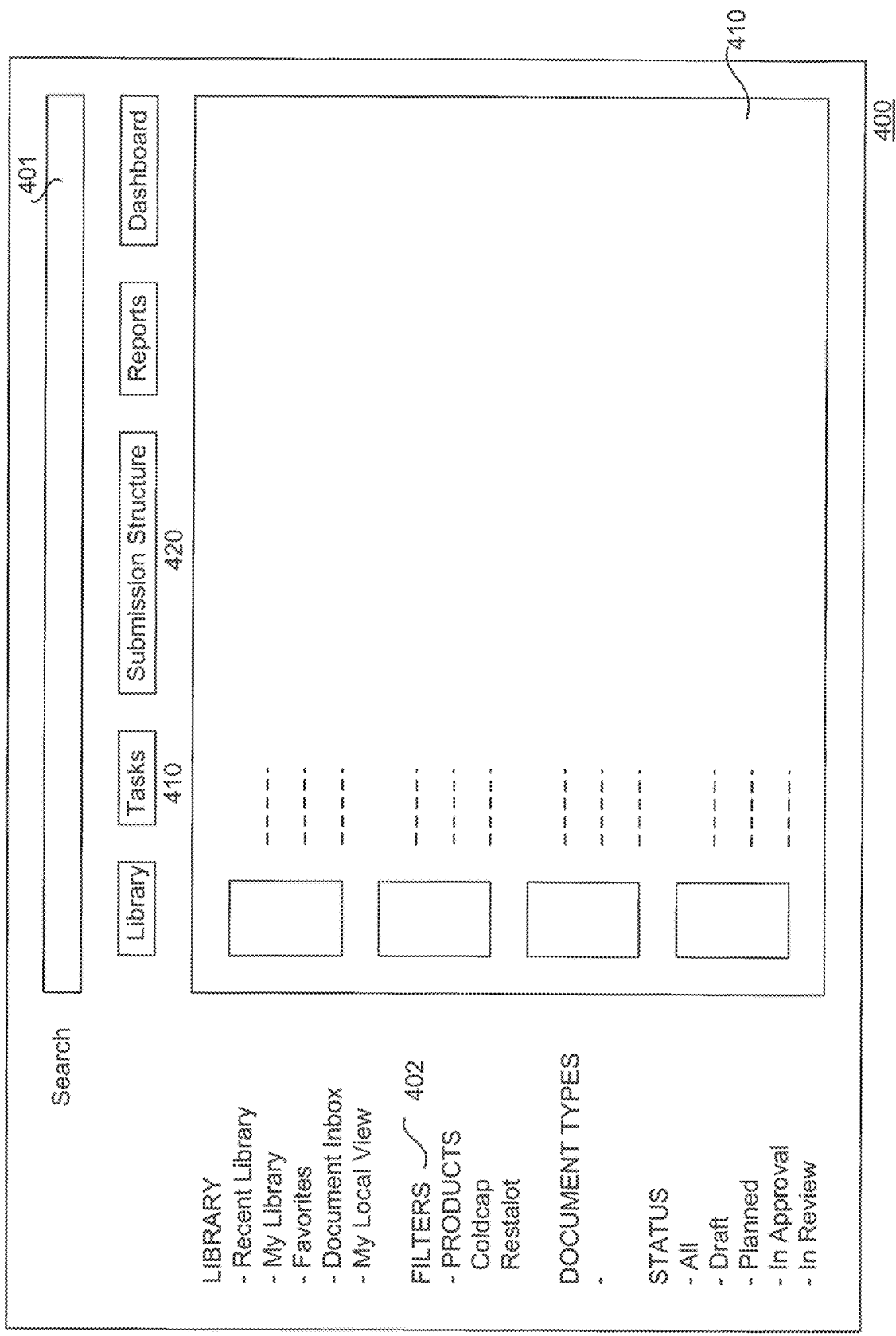
FIG. 4 illustrates an example submission user interface according to one embodiment of the present invention.
Figure 5:
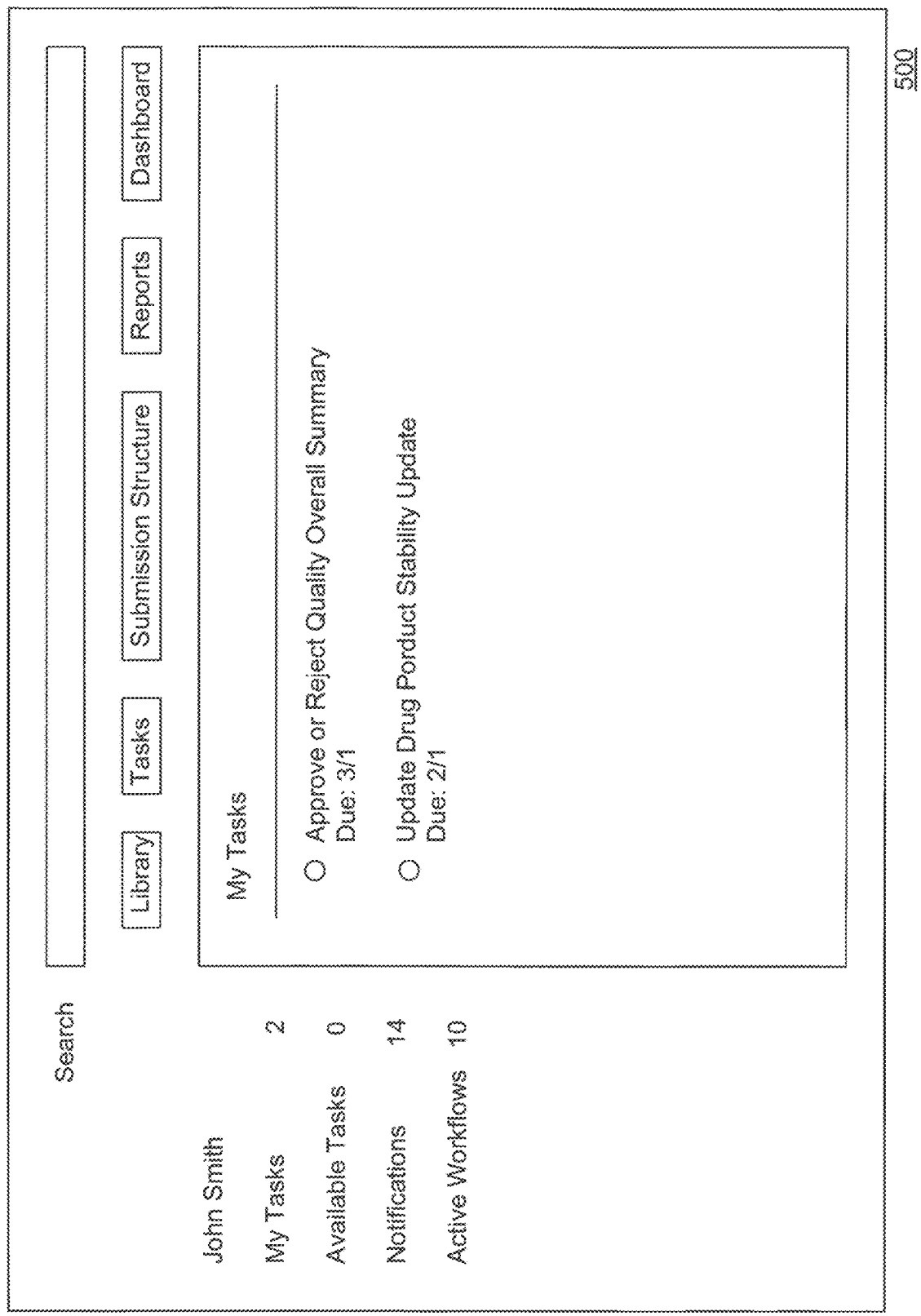
FIG. 5 illustrates an example task user interface according to one embodiment of the present invention.
Figure 6:
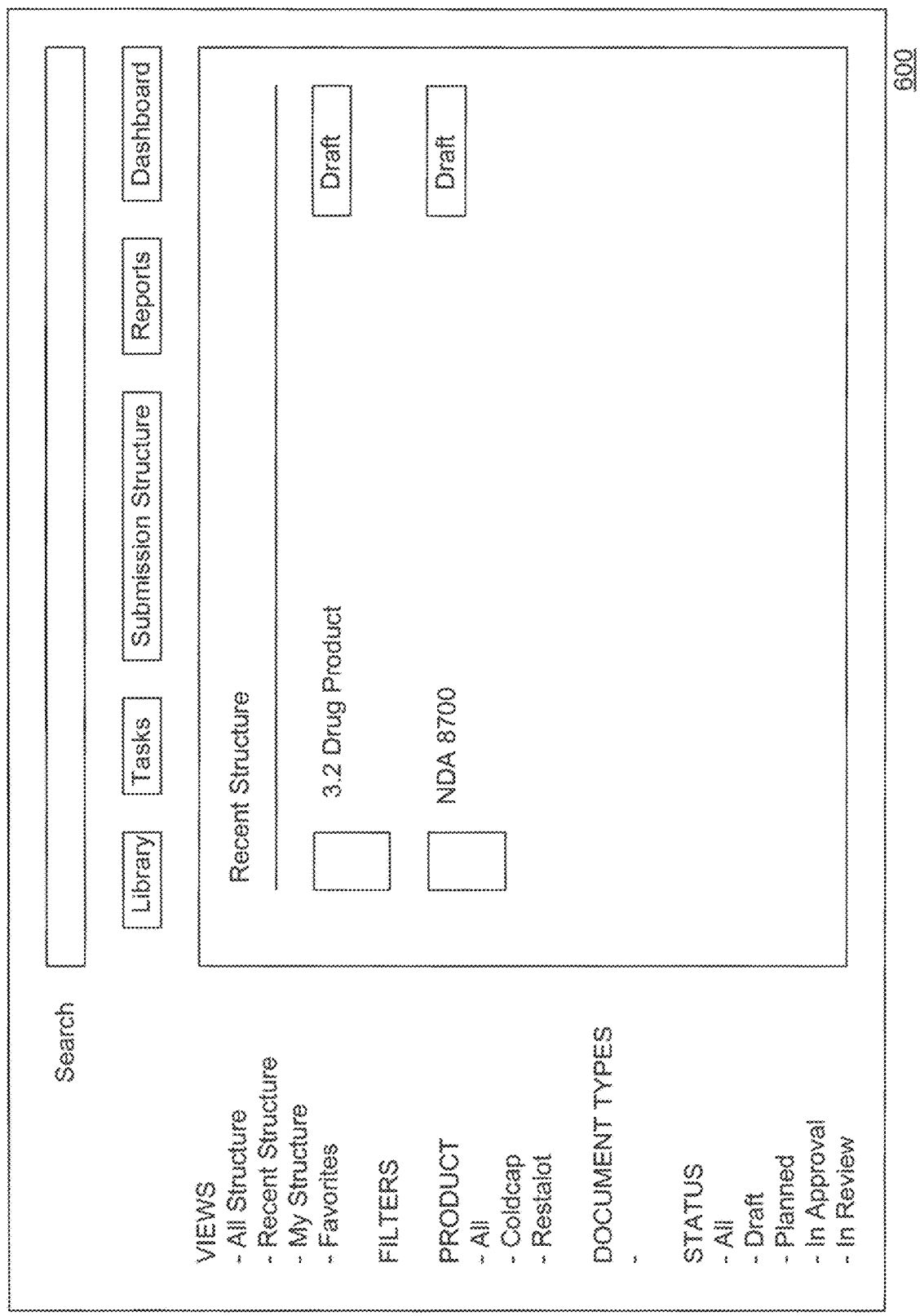
FIG. 6 illustrates an example submission structure user interface according to one embodiment of the present invention.

FIG. 3 illustrates an example high level block diagram of the content management server 112 according to one embodiment of the present invention. The content management server 112 may be implemented by the computing device 200, and may have a processing unit 1121, a system memory 1122, an input device 1123, an output device 1124, and a network interface 1125, coupled to each other via a system bus 1126. The regulatory information management module 114 may be stored in the system memory 1122. The regulatory information management module 114 may have a submission controller 1141, a registration controller 1142, a submission archive controller 1143, a validation controller 1144, a publishing controller 1145 and a gateway interface 1146.

The submission controller 1141 may generate a submission user interface 400 for the user to search the submission library. The user may find information he is looking for (e.g., a drug documentation related to a product) through searching via a search window 401, or filtering via filters 402. The user may also search for information specific to a geographic region, e.g., by selecting My Local View. The user interface 400 may have a window 410 for displaying documents based on the search result. In one implementation, submission is based on the drug information association ("DIA") reference model, and the reference model classification is built based on the latest DIA standards.

When the user clicks on a Task tab 410 on the user interface 400, a task user interface 500 may be displayed, and the user may work on his/her tasks, e.g., participating review and approval flow works.

The submission controller 1141 may also manage submission structures (e.g., a New Drug Application ("NDA") submission structure, or a Biological License Application ("BLA") submission structure). When the user clicks on the Submission Structure tab 420 on the user interface 400, a submission structure interface 600 may be displayed. One or more submission structures may be shown on the submission structure interface 600, e.g., an NDA.

If the user selects one of the submission structures, e.g., NDA 8700, a user interface 700 for that submission structure may be displayed, which may include the hierarchy of the documentation, e.g., Administrative Information, Common Technical Document Summaries, Quality, Nonclinical Study Reports, and Clinical Study Reports. The submission structure may serve as materials for the submission. The submission structure may include placeholder documentation for expected documents, and link documents from repositories in the content storage system 111 directly into the submission structure. In one example, the user may want to add a clinical overview from the existing set of documentation. He may search for it in the content storage system 111 and drag it to the submission structure. The user may also add a link or reference of content from other repositories directly into the structure.

Figure 8:
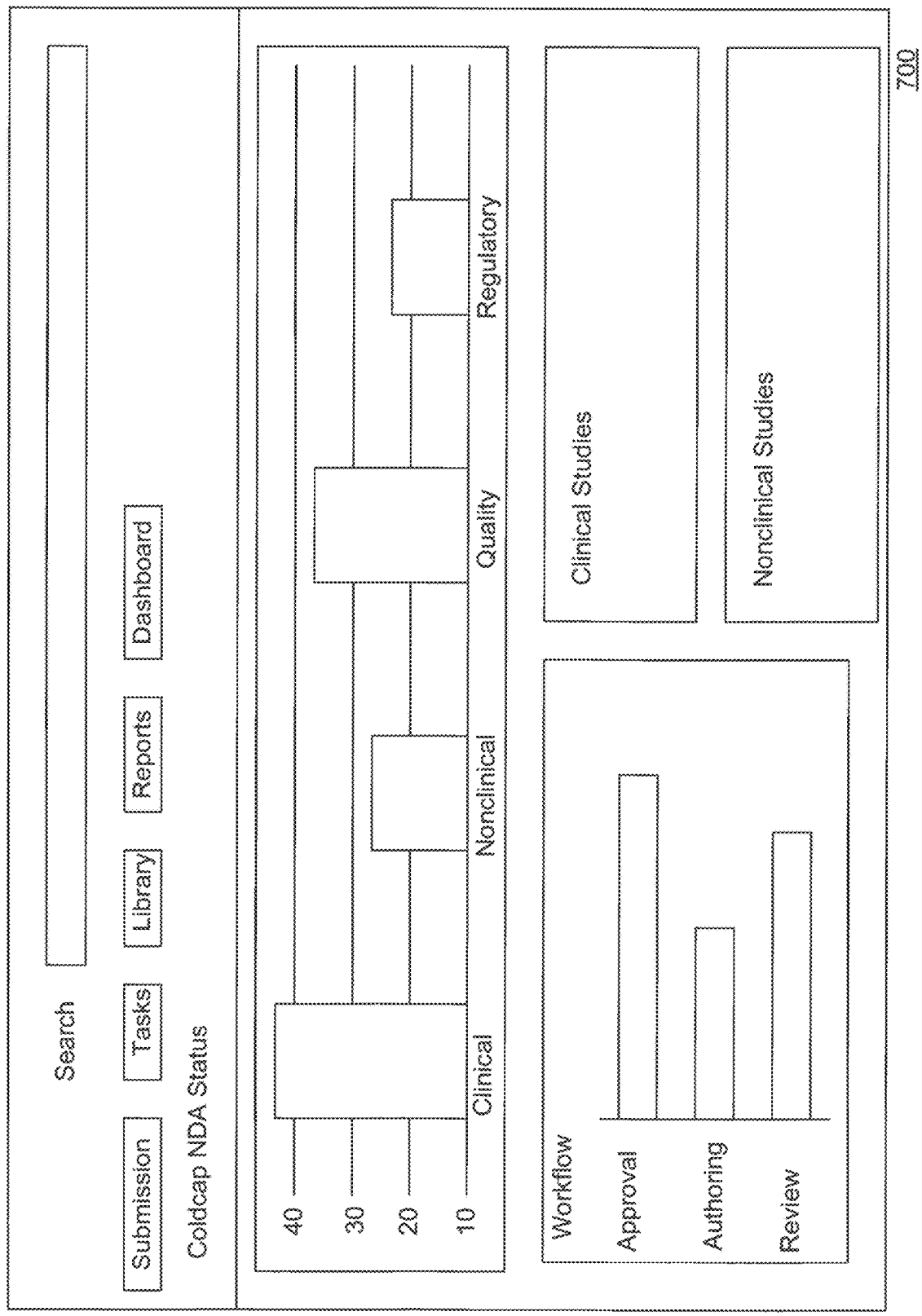
FIG. 8 illustrates an example dashboard report user interface according to one embodiment of the present invention.

Through the process of structure assembly and management of content, the submission controller 1141 may also provide dashboard reports to give users the ability to manage the overall process through structure assembly and management of the content. As shown in FIG. 8, the dashboard report may include current status of the NDA filing, in terms of documentation, a quick look of the status of the documents, each major module, as well as any workflows. From the dashboard, users may click into any of the wedges, and be taken to the report results. From the report results, users may take actions on the documents themselves.

The submission controller 1141 may continuously monitor documents in the content storage system 111 for any changes that might affect publishing. The submission controller 1141 may also monitor the submission plan.

The registration controller 1142 may provide a powerful tool for getting visibility to global registration information, and take actions on regulatory events. All tied seamlessly with various information and functions provided by the content management system 110. The registration controller 1142 may manage registration, product and application information to help customers to make informed decisions about their business. The registration controller 1142 may display registration, product and application information on a user interface 900. If a user wants to understand the global footprint of a product Coldcap, he may click on the Report button on the user interface 900. The user interface 1000 may be presented, displaying global registrations and their status in one report. The reports are actionable, allowing users to drill in a specific registration, e.g., the AU Coldcap 390 registration. The registration record may provide key information including the register information, the associated product information, application date, and key registration dates. The registration record may be displayed on a separate user interface. Information in the registration record may be based on the IDMP data model. The registration controller 1142 may display a user interface for receiving product registration information and updates. The registration controller 1142 may further provide a comprehensive ability to not only capture and view regulatory data, but also take actions when an event occurs, including the ability to assess the impact of change, and manage global response to such change.

In addition to provide registration information, the registration controller 1142 may allow users to take actions on the regulatory business. Users may initiate an action through an event (e.g., update the Coldcap shelf life to 30 months), and assign activities to that event. The activities may be acted on by regulatory personnel that are responsible for a market. Activities may include submission responses. The user can also view the associated submission to address the activity.

Users may trace an actual submission binder representing the submissible content managed in submission library. User may also see key related content and data, such as correspondence and commitment made by the basis for the submission.

The registration controller 1142 may provide powerful, cloud based capabilities to manage product registration information and health authority interactions globally, and robust abilities to capture, view and take actions upon product registrations. It may track bidirectional interactions with health authorities globally, including correspondence, commitments and queries. With the related data features of the content management system 110, it may relate actions to be taken to product registrations. Since it is cloud based, it may tear down the virtual walls that often exist between centralized regulatory teams and their affiliates. Typically, the registration controller 1142 allows users at local sites to access and capture data related to their registration, while have visibilities into and collaborate with teams globally.

In one implementation, the registration controller 1142 is based upon the new Identification of Medicinal Products ("IDMP") data standard for product data, and can support an interface that allows regulatory groups to standardize their registration data, while also make it easy to interface with other software applications.

The registration controller 1142 may help to improve data quality, and make it easy to collaborate with global partners, affiliates and authorities, while reducing duplication and discrepancies by providing a single centralized depository for capturing and sharing regulatory data. The registration controller 1142 may also provide robust reporting and dashboard, and make it easy to report on, and visualize key data points, such as marketing status, registration details and marketing details.

The submission archive controller 1143 may provide a powerful, cloud based capability to access a complete history of regulatory submissions and correspondence globally, with an easy to use interface. From the upload and view perspective, the submission archive controller 1143 may provide electronic common technical document ("eCTD"), non-eCTD electronic, paper and PDF submissions. With the powerful search and filter capabilities of the content management system 110, the submission archive controller 1143 may make document and data search fast and easy. Upon import, all navigation within and outside of documents is rendered to be fully navigable in the content management system 110, making it easy to follow references. In addition, there is a built-in viewer. For eCTDs, it allows users to view submissions in a current view, sequentially, or as cumulative document views.

The submission archive controller 1143 works globally. Given that it is cloud based, it may provide a centralized archive for sharing global filings across the enterprise without requiring any additional software. In addition, with its powerful, easy to use searching and filtering capability, the submission archive makes it easy to find previously submitted information, in order to respond quickly to internal and external queries.

Figure 12:
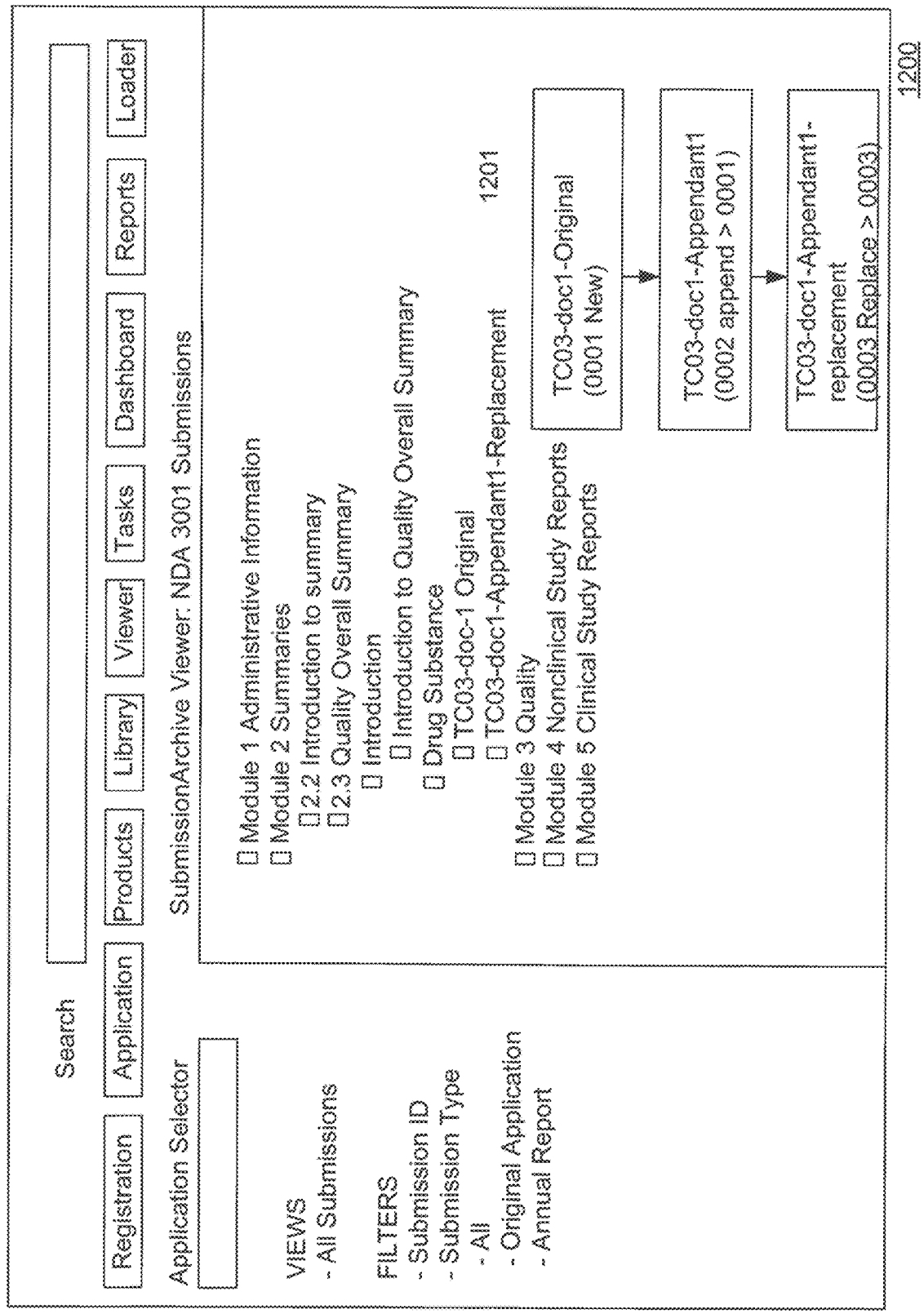
FIG. 12 illustrates an example submission archive user interface according to one embodiment of the present invention.

The submission archive controller 1143 may assist the process from submission planning to content authoring and publishing, by storing and viewing published output. The submission archive controller 1143 may display user interfaces in FIG. 11 and FIG. 12 for users to search and see the previously submitted information. As shown in FIG. 11, users can navigate to the viewer tab and select the application to view. Through the viewer, the user and navigate to published output, and get information on published facts. For a summary document, users can see published info from the backbone, and also historical context, as shown in FIG. 12. Users can view the output the content management system 110, and use the native navigation of the document, including bookmarks and cross document hyperlinks.

In previous solutions, published output resides on uncontrolled file drives, disconnected from the source content. The submission archive controller 1143 addresses the need to securely map published output while providing global accessibility by storing the published output and allowing users to access the published output.

The validation controller 1144 may enable continuous and incremental validation of submission documents. Validation is a part of the publishing process. Every health authority has certain validation rules that the submissions need to be abide by. For example, values need to be in XML files, and fields need to be made available in a certain format. The validation controller 1144 may continuously validate submission documents and display validation results during the authoring process, so that users can correct errors during the authoring process, instead of waiting for the end of the authoring process.

The present invention provides a method for breaking up validation into smaller tasks as the submission is assembled and content becomes available. This may provide users with information about validation errors and warnings earlier in the process. On a submission record, users may set a corresponding regional version (e.g. DTD/XSD, schema files provided by a health authority and defining what the XML should conform to) and a validation criterion version applicable for the regional version. The validation criterion version is used to determine which rules are applicable for the corresponding submission. As new validation criteria become available, users can choose to adopt the new version or retain use of a prior version that is still accepted during an overlap period.

Structural validation rules may be verified as the content plan is created to become the structure within a submission archive in the content storage system 111 and as the XML files are created. Validation results may be captured at the XML document, element and attribute level. From the content plan and submission archive document and section, users may view the corresponding validation results.

File validation rules may be verified as the source content is published from the content plan item to become published documents within the submission archive. Validation results may be captured at the document, page, bookmark, link or link coordinates. From the content plan item and submission archive published documents, users may view the corresponding validation results and act.

Validation criteria may be stored in an object in the content management system 110 as system managed information to provide visibility to users while keeping the records managed to allow for updates as new validation criteria are issued and to allow administrators to inactivate validation criteria deemed to be not applicable. With the release of new validation criteria, the records may be provisioned to a repository in the content storage system 111 as inactive for users to activate when they are ready to do that. In one embodiment, validation criteria may be stored based on health authority, version and applicable DTD/XSD. In one embodiment, validation criterion version may be captured on each record and sourced from a controlled vocabulary object.

A Submission Validation Criterion object may be used to store each validation criterion as published by the health authority. This may contain a combination of system managed fields (e.g., Health Authority code) and user editable fields (e.g. Corrective Action). Each validation criterion may have version specific information and a relationship with the applicable geographic region, country and health authority.

A Submission Validation Result object may be used to capture details of the validation results with the relationship to the submission, content plan, content plan item, source document, published document and node within the submission archive in the content storage system 111.

In one embodiment, on a submission record, users may specify a regional DTD/XSD version and a corresponding validation criterion version. Only validation criterion that is active and corresponds with the regional DTD/XSD version can be applied. Content Plan and Content Plan Item records may have the Continuous Validation field set to "Yes".

Continuous validation may be performed when the Continuous Validation field is set to "Yes", a Content Plan record is created or updated, a publishing job is initiated, or documents are published from the content plan.

On-demand validation may be performed from an action on submission, content plan or content plan item. For a submission, validation may be performed for the entire submission. For a Content Plan, validation may be performed for the section, descendants, content plan items and published documents. For a Content Plan item, validation may be performed for the specific content plan item and published documents.

Once validation is performed to compare structure and format of data with the validation criteria, the validation results may be stored in a validation result object depicting the completed validation and unresolved validation. The validation results may span the submission, Content Plan, Content Plan item and published output. Validation results may include a reference to the validation code, application, submission, Content Plan, Content Plan item and published file. When validation is successfully performed against a submission, content plan section, content plan item or published document, an entry may be created within the Validation Result object with a reference to the validated item, validation code and with a lifecycle state of "successful". When validation is unsuccessful for a submission, content plan section, content plan item or published document, an entry may be created within the Validation Result object with a reference to the validated item, validation code, failure detail and with a lifecycle state of "Unsuccessful". An example of an unsuccessful validation result is shown in FIG. 13. When an entry is no longer relevant because validation has been re-processed, the records may be set to a lifecycle state of "superseded" and a status of inactive.

When new validation criteria are supported in the content management system 110, the validation rules may be made available as new records, and the validation version may be made available.

Validation through the submission publishing process may allow users to verify the validity of a submission and reconcile results within a single system, e.g., the content management system 110. Customers may continuously and incrementally validate nodes based on changes as content is updated (e.g., when new documents are published), or on-demand as an action from the submission record.

The publishing controller 1145 may control continuous publishing of documents to the submission archive when they are authored. As parts of the submission are completed, they are continuously published for review, instead of being published only when the authoring process is completed. Users may correct errors timely during the authoring process, rather than waiting for the end of the authoring process. Consequently, the time between the user needs to do a submission and the actual submission may be minimized.

The gateway interface 1146 may enable submissions to be submitted directly to the health authority gateway 130.

In one implementation, the regulatory information management system may use the same data model for data objects for submission, product registration, submission archive, and source document management, and share data (e.g., product information and manufacturer information) among these functions, so as to avoid duplicate data entry, management and tracking. Health authorities define data requirements, and the regulatory information management system may provide information about the health authority data requirements. Customers may decide the data and documents to submit based on the information about the health authority data requirements, depending on the type of the submission. An example data model for Product is shown below. The bolded names are the objects in the system, in italics are the actual names of the records.

Product—Cold medicine (this is a generic name)
Drug Products
    DP1—Coldcap A (this is the marketed name)
    Product Details (this is how it's sold. Each one of these could be manufactured by a different manufacturer, and could contain different active substances or inactive ingredients)
        45 mg vial
        45 mg tablet
        90 mg vial
        90 mg tablet
    DP2—Coldcap B
    Product Details
        30 mg capsule
        60 mg capsule The system of the present invention unites contributors, partners, and affiliates in the cloud with a single destination for regulatory documents. Global and regional submission dossiers harmonize planning and provide real-time visibility into submission readiness. Globalizing processes becomes substantially easier with a single authoritative source for submissions content. Global alignment may maintain greater control over the distribution and tracking of documents that affiliates submit to local authorities. The system may track the progress of documents through actionable reports and dashboards, mitigating risks to submission timelines, and enabling continuous visibility of the documents. The system may eliminate manual processing to speed submission assembly and improve SOP compliance and speed to market globally. It may automate tracking and reporting by authoring, exchanging, and assembling documents directly within the content management system 110.

Figure 14:
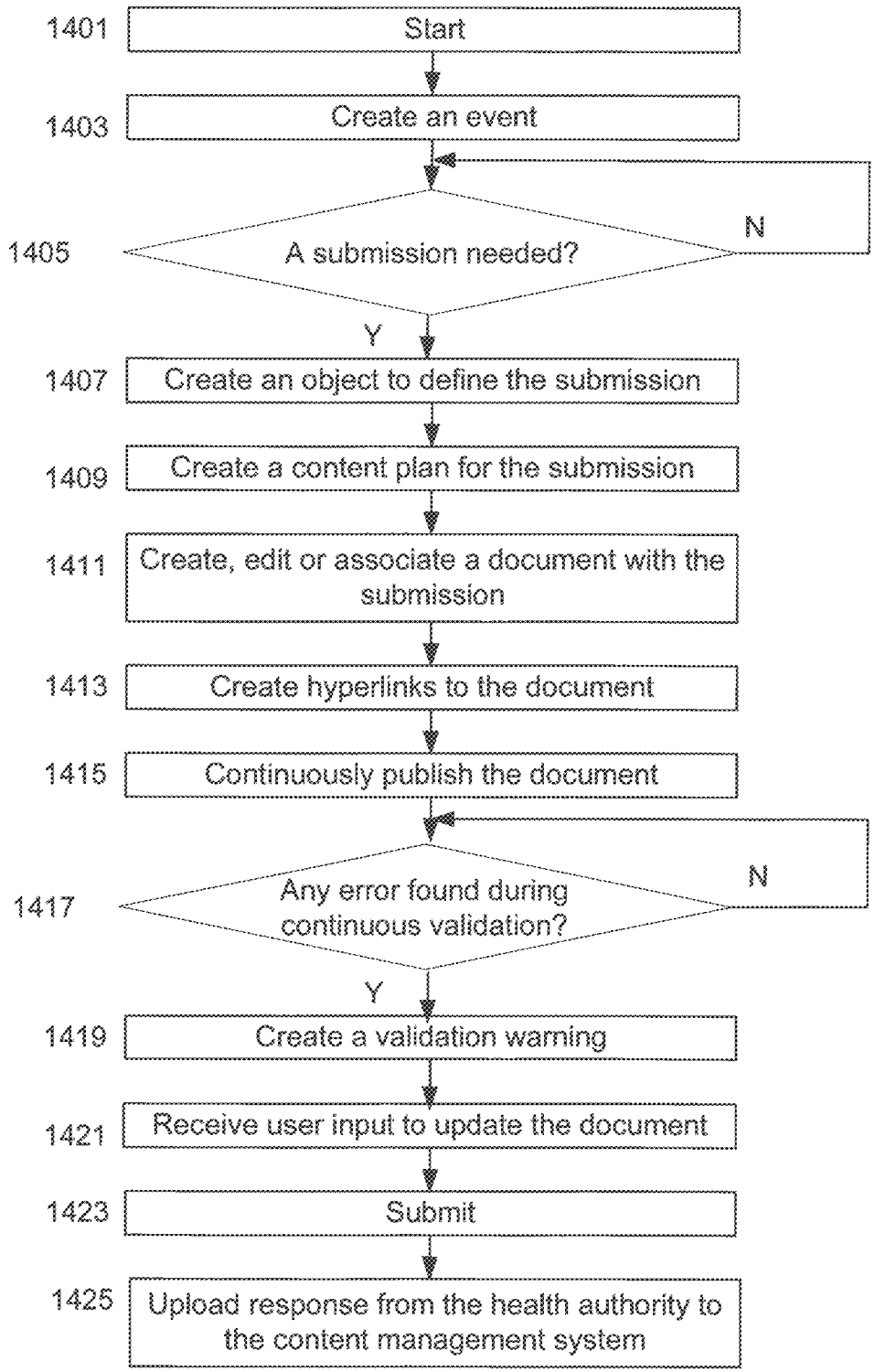
FIG. 14 illustrates an example flowchart of a submission publishing process according to one embodiment of the present invention.

FIG. 14 illustrates an example flowchart of a submission publishing process according to one embodiment of the present invention. The process may start at 1401.

At 1403, an event may occur and be created in the content management system 110. The event may be, e.g., a new product is introduced or a change/variation occurs to an existing product.

At 1405, based on the type of change, a regulatory review may be performed to determine if a submission is needed. An activity may be created in the content management system 110 to track the decision process.

If a submission is needed, a submission process may start at 1407, creating objects to define the submission, e.g., with the submission controller 1141. In one example, regulatory objective, submission and associated information (e.g., Clinical Study joins) may be created in the content management system 110. Joins may be created and submission metadata may be set as well.

Each submission type may require different content to be submitted to a health authority. A plan may be created for the content based on the change, e.g., with the submission controller 1141, at 1409. In one embodiment, a Content Plan may be created in the content management system 110 from a Template, with Constraints assisting in the selection of Content Plan sections/items to include.

Based on the content needed for the submission, documents may need to be authored, or may have already been authored and need to be associated with the submission, e.g., with the submission controller 1141, at 1411. The documents may go through a review cycle. In one embodiment, documents in the content management system 110 may be matched to the Content Plan Items, and locked to a specific version. Continuous Publishing and Validation is enabled.

At 1413, hyperlinks to documents associated with the submission may also be created, e.g., with the submission controller 1141.

At 1415, submission documents may be continuously published to the submission archive, e.g., with the publishing controller 1145.

At 1417, the submission documents may be continuously validated against validation criteria, e.g., with the validation controller 1144.

If there is an error, a validation warning may be created, e.g., with the validation controller 1144, at 1419.

The user may review the validation results, as well as comments from reviewers of the Published Output, updates may be made to the documents in the submission and received by the submission publishing controller 1145 at 1421. In one embodiment, Content Plan Items may be published and validated continuously as updates are made, without user interactions which may include, e.g., downloading documents, uploading documents, requesting for validation or requesting for publishing.

Once content is finalized and is ready for submission, Continuous Publishing and Validation may be turned off, the published output may be submitted, or uploaded, to the gateway 130 at 1423.

At 1425, responses from the gateway 130 may be monitored and uploaded into the content management system 110.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

In this specification, the term "software" is meant to include firmware residing in read-only memory or applications stored in magnetic storage, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs. Examples of computer programs or computer code include machine code, for example is produced by a compiler, and files including higher-level code that are executed by a computer, an electronic component, or a microprocessor using an interpreter.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more.

What is claimed is:

1. A method for managing submission of a document with a content management system, wherein the content management system comprises a content management server and a plurality of repositories, the method comprising:
creating an event in the content management system in response to a change to a regulated product;
assessing impact of the change to the regulated product;
creating an activity in the content management system to track a process for determining if a first submission to an authority regulating the regulated product is needed based on a type of the change to the regulated product;
receiving a user input that the first submission to the authority regulating the regulated product is needed based on the type of the change to the regulated product;
creating a first object in the content management system to define the first submission when the first submission is needed;
creating a first content plan for the first submission to the authority regulating the regulated product in the content management system to define content to be submitted to based on the change to the regulated product;
associating a first component, which is in the scope of the defined content to be submitted, with the first submission;
publishing the first component of the first submission to an archive in the content management system; and
validating the first component against a first validation criterion, wherein the first validation criterion is based on a regulatory requirement for the regulated product.

2. The method of claim 1, further comprising:
associating a second component, which is in the scope of the defined content to be submitted, with the first submission;
publishing the second component of the first submission to the archive in the content management system; and
validating the second component against a second validation criterion, wherein the second validation criterion is based on a regulatory requirement.

3. The method of claim 1, wherein the event comprises introduction of a new product.

4. The method of claim 1, wherein the event comprises a change to an existing product.

5. The method of claim 1, further comprising: creating an activity in the content management system for determining if the first submission is needed.

6. The method of claim 1, further comprising: receiving an input on a new component associated with the first submission in the content management system.

7. The method of claim 1, further comprising: receiving revisions to an existing component associated with the first submission in the content management system.

8. The method of claim 1, further comprising: matching an existing document in the content management system to the first submission.

9. The method of claim 1, further comprising: creating a hyperlink to a document associated with the first submission in the content management system.

10. The method of claim 1, further comprising: receiving a first update to the first component in response to a first validation result.

11. The method of claim 10, further comprising: continuously publishing the updated first component to the archive in the content management system after receiving the first update to the first component.

12. The method of claim 10, further comprising: continuously validating the updated first component in the content management system after receiving the first update to the first component.

13. The method of claim 1, further comprising: generating a validation warning when there is an error.

14. The method of claim 1, further comprising: uploading the first submission from the content management system to an electronic gateway over a network in response to a user input.

15. The method of claim 14, further comprising: monitoring response from the electronic gateway.

16. The method of claim 15, further comprising: storing the response from the electronic gateway to the content management system.

17. A system for managing submission of a document, comprising:
a plurality of repositories for storing content related to the submission; and
a registration controller for assessing impact of a change to a regulated product, and enabling an activity in the content management system to track a process for determining if a first submission to an authority regulating the regulated product is needed based on a type of the change to the regulated product;
a content management server comprising:
a submission controller for creating an event in response to the change to the regulated product; receiving a user input that the first submission to the authority regulating the regulated product is needed based on the type of the change to the regulated product; creating a first object to define the first submission when the first submission is needed; creating a first content plan for the first submission to the authority regulating the regulated product to define content to be submitted based on the change to the regulated product; and associating a first component, which is in the scope of the defined content to be submitted, with the first submission;
a publishing controller for publishing the first component of the first submission to an archive in a repository; and
a validation controller for validating the first component against a first validation criterion, wherein the first validation criterion is based on a regulatory requirement for the regulated product.

18. The system of claim 17, further comprising a gateway interface for uploading the first submission to an electronic gateway over a network in response to a user input.

19. The system of claim 17, wherein the submission controller further creates a hyperlink to a document associated with the first submission in the content management system.

20. The system of claim 17, wherein the submission controller further generates a validation warning when there is an error.

* * * * *